(12) United States Patent
Liu

(10) Patent No.: US 11,938,078 B2
(45) Date of Patent: Mar. 26, 2024

(54) INTERACTIVE SEX TOY WITH SENSORY FEEDBACK

(71) Applicant: HYTTO PTE. LTD., Singapore (SG)

(72) Inventor: Dan Liu, Guangzhou (CN)

(73) Assignee: HYTTO PTE. LTD., Singapore (SG)

( * ) Notice: Subject to any disclaimer, the term of this patent is extended or adjusted under 35 U.S.C. 154(b) by 0 days.

(21) Appl. No.: 17/717,917

(22) Filed: Apr. 11, 2022

(65) Prior Publication Data
US 2022/0233396 A1    Jul. 28, 2022

Related U.S. Application Data

(63) Continuation of application No. 16/352,876, filed on Mar. 14, 2019, now Pat. No. 11,311,453.

(51) Int. Cl.
*A61H 19/00* (2006.01)
*A61F 5/41* (2006.01)
*A61H 23/02* (2006.01)

(52) U.S. Cl.
CPC .............. *A61H 19/44* (2013.01); *A61F 5/41* (2013.01); *A61H 19/34* (2013.01); *A61F 2005/417* (2013.01); *A61H 23/02* (2013.01); *A61H 2201/5007* (2013.01); *A61H 2201/5071* (2013.01); *A61H 2201/5097* (2013.01)

(58) Field of Classification Search
CPC ........ A61H 19/00; A61H 19/30; A61H 19/32; A61H 19/34; A61H 19/40; A61H 19/44; A61H 2201/5007; A61H 2201/5071; A61H 2201/5097; A61F 5/41
See application file for complete search history.

(56) References Cited

U.S. PATENT DOCUMENTS

| 3,361,130 A | 1/1968 | Rowe |
| 5,807,287 A | 9/1998 | Cheng |
| 6,277,085 B1 | 8/2001 | Flynn |
| 6,368,268 B1 * | 4/2002 | Sandvick ............... A61H 19/32 600/38 |

(Continued)

FOREIGN PATENT DOCUMENTS

| KR | 101256565 B1 | 4/2013 |
| WO | 2006040750 A1 | 4/2006 |
| WO | 2008067487 A2 | 6/2008 |

*Primary Examiner* — Christine H Matthews
(74) *Attorney, Agent, or Firm* — McCarter & English, LLP; James M. Smedley; Alex Korona

(57) ABSTRACT

An interactive sex toy with sensory feedback is described herein. The sex toy may include a main body upper shell, a main body lower shell, and several trigger buttons, wherein the four trigger buttons are encased in the main body shell. Each of the four trigger buttons may include a mechanical spring and a conductive foam plastic. A motor maybe activated on a condition that at least one of the four trigger buttons is depressed. A pressure level may increase when an additional trigger button is depressed. A method for using an interactive sex toy with sensory feedback may include receiving physical pressure readings from an interactive sex toy with sensory feedback at a first device, converting the physical pressure readings to pressure parameter instructions, transmitting the pressure parameter instructions to a second device, and actuating a sex toy with the pressure parameter instructions.

17 Claims, 13 Drawing Sheets

(56) References Cited

U.S. PATENT DOCUMENTS

| | | | |
|---|---|---|---|
| 8,255,299 B2 * | 8/2012 | Cambridge | G06Q 20/085 |
| | | | 600/38 |
| 8,644,967 B2 | 2/2014 | Seiler | |
| 8,936,544 B2 * | 1/2015 | Shahoian | A61H 19/32 |
| | | | 600/38 |
| 9,762,515 B1 | 9/2017 | Olivares et al. | |
| 10,051,328 B2 | 8/2018 | Olivares, II et al. | |
| 10,218,795 B1 | 2/2019 | Messinger | |
| 10,576,013 B1 | 3/2020 | Sloan | |
| 11,134,041 B1 | 9/2021 | He | |
| 2002/0065477 A1 | 5/2002 | Boyd et al. | |
| 2002/0133103 A1 * | 9/2002 | Williams | A61H 19/50 |
| | | | 601/46 |
| 2003/0036678 A1 * | 2/2003 | Abbassi | A61H 19/40 |
| | | | 340/407.1 |
| 2004/0082831 A1 * | 4/2004 | Kobashikawa | A61H 19/32 |
| | | | 600/38 |
| 2004/0097852 A1 | 5/2004 | Boyd et al. | |
| 2005/0138560 A1 * | 6/2005 | Lee | H04N 21/47202 |
| | | | 715/201 |
| 2006/0247561 A1 | 11/2006 | Chiu | |
| 2012/0259171 A1 | 10/2012 | Shmakov | |
| 2012/0304216 A1 | 11/2012 | Strong | |
| 2013/0165747 A1 | 6/2013 | Maggs | |
| 2014/0011557 A1 | 1/2014 | Coyle | |
| 2014/0115690 A1 | 4/2014 | Huang et al. | |
| 2016/0049043 A1 | 2/2016 | Tennenhaus et al. | |
| 2017/0119619 A1 | 5/2017 | Dills | |
| 2018/0116904 A1 | 5/2018 | Lieberman et al. | |
| 2019/0133877 A1 | 5/2019 | Cambridge | |
| 2020/0009009 A1 | 1/2020 | Nishida | |
| 2020/0276504 A1 | 9/2020 | Liu | |
| 2020/0289363 A1 | 9/2020 | Liu | |
| 2020/0315908 A1 | 10/2020 | Liu | |
| 2020/0366972 A1 | 11/2020 | Sloan | |
| 2021/0341992 A1 | 11/2021 | Cambridge | |
| 2022/0141550 A1 | 5/2022 | Liu | |

* cited by examiner

INTERACTIVE SEX TOY WITH SENSORY FEEDBACK

CROSS REFERENCE TO RELATED APPLICATION

This application is a continuation of U.S. patent application Ser. No. 16/352,876, filed on Mar. 14, 2019, which is hereby incorporated by reference in its entirety.

FIELD OF INVENTION

Embodiments of the present invention are in the field of sex toy. Specifically, embodiments of the present invention are related to sex toys capable of providing sensory feedback.

BACKGROUND

Female and male masturbation, are explained as the stimulation of the genital organs with the goal of obtaining pleasure, and the possibility of reaching climax. Generally it is understood as self-sexual intercourse, although it could be performed towards someone else's genitals with the same purpose.

Marital or sexual aids (commonly referred to as "sex toys") have been known and used throughout the centuries by both men and women. Sexual pleasure, climax or orgasm is frequently a desired result of sexual activity, whether interpersonal or autoerotic.

Generally, sex toys are either used alone or with a partner. There exists a need to be able to engage in sexual climax with a partner by having a second sex toy react to the usage of a first sex toy and vice versa.

SUMMARY

An interactive sex toy with sensory feedback is described herein. The sex toy may include a main body upper shell, a main body lower shell, and a series of trigger buttons (e.g., four trigger buttons in one preferred embodiment), wherein the series of trigger buttons are encased in the main body upper shell or in the main body lower shell. In other embodiments, wherein the series of trigger buttons are partly in the main body upper shell and the main body lower shell (for example, some of the trigger buttons may be on the main body upper shell, the rest may be on the main body lower shell). The arrangement of the series of trigger buttons may be symmetrical or staggered (for example, symmetrical arrangement may mean that when the sex toy is thrusting into a woman or man's body, two buttons, one of which is in the main body upper shell and the other is in the main body lower shell may be triggered at the same time and stagger arrangement means when the sex toy is thrusting into a woman or man's body, all of those trigger buttons may be triggered one by one). Each of the trigger buttons may include an engagement means, such as a mechanical spring and a conductive foam plastic. A motor maybe activated on a condition that at least one of the trigger buttons is engaged, such as being depressed. A pressure level may increase when an additional trigger button is engaged.

A method for using an interactive sex toy with sensory feedback may include receiving physical pressure readings from an interactive sex toy with sensory feedback at a first device, converting the physical pressure readings to pressure parameter instructions, transmitting the pressure parameter instructions to a second device, and actuating a sex toy with the pressure parameter instructions.

BRIEF DESCRIPTION OF THE DRAWINGS

A more detailed understanding may be had from the following description, given by way of example in conjunction with the accompanying drawings wherein.

DETAILED DESCRIPTION

Figure 1:
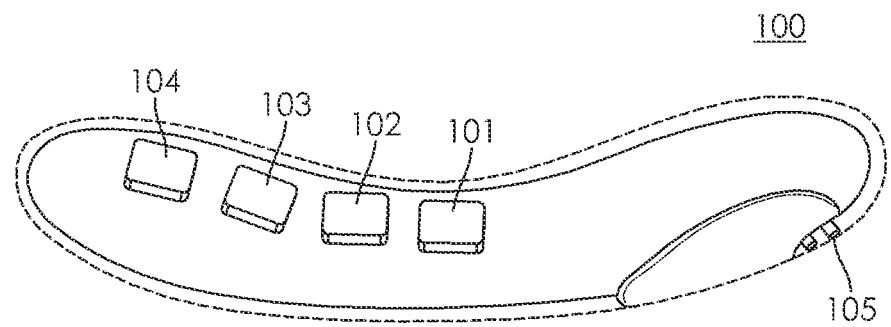
FIG. 1 is an illustration of a sex toy with sensory feedback, in accordance with at least one embodiment of the present invention.

In the description above, the detailed description, the claims below, and in the accompanying drawings, references is made to particular features (including method steps) of the various embodiments of the invention. It is to be understood that the disclosure of the invention in this specification includes all possible combinations of such particular features, for example, where a particular feature is disclosed in the context of a particular aspect or embodiment of the invention, or a particular claim, that feature can also be used, to the extent possible, in combination with and/or in the context of other particular aspects and embodiments of the invention, and in the invention generally.

The embodiments of the present invention can be implemented in a variety of ways, such as a process, an apparatus, a system, a composition of matter, a computer readable medium (for example, a computer readable storage medium), or a computer network wherein program instructions are sent over optical or electronic communication links. In this specification, these implementations, or any other form that the invention may take, may be referred to as techniques. In general, the order of the steps of disclosed processes may be altered within the scope of the invention.

A detailed description of one or more embodiments of the invention is provided below along with accompanying figures that illustrate the principles of the invention. The invention may be described in connection with such embodiments, but the invention is not limited to any particular embodiment or any particular set of such embodiments. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

An interactive sex toy with sensory feedback may be described herein. In a preferred embodiment of the present invention, as the sex toy is inserted into a user's vagina, anus or other cavity, the sex toy is configured to be able to feel/detect the pressure on different points. The vibrations may react according to the strength of pressure, based on pre-defined settings. The settings may also be programmable by a user, such as via a wired or wireless connection to a controller or computing device (e.g., smart phone). For example, the deeper the sex toy is inserted into a cavity, activating more pressure points, the device may be configured to generate stronger vibrations. In other examples, the pressure points may detect contractions in the cavity, which may indicate increased stimulation, excitement or arousal in the user, and be configured to generate stronger or tailored vibrations in response to such detected pressure variations.

According to an embodiment of the present invention, a pressure sensor from the sex toy may be configured to send a signal to a second toy (e.g., a second sex toy in use by a second user). For instance, the second toy may be configured to react to the pressure detected by the first sex toy (e.g., depth of insertion of the first sex toy).

FIG. 1 is an example of a sex toy with sensory feedback. In this exemplary embodiment, the sex toy 100 may have four trigger buttons 101, 102, 103, and 104. Additionally, the sex toy 100 may have a printed circuit board (PCB) with conductive needles 105 (use for connecting a charging line). Alternative embodiments may utilize additional or fewer trigger buttons, or alternative control means other than a PCB, and embodiments of the present invention are contemplated for use with any number of trigger buttons, or types of control means. Further, while for the purpose of description here, the triggers buttons are individual buttons, in alternative embodiments, other sensors could be used, such as capacitive sensors or pressure pads. One of ordinary skill in the art would appreciate that there are numerous types of sensors that could be used with embodiments of the present invention, and embodiments of the present invention are contemplated for use with any appropriate type of sensor.

Figure 2A:
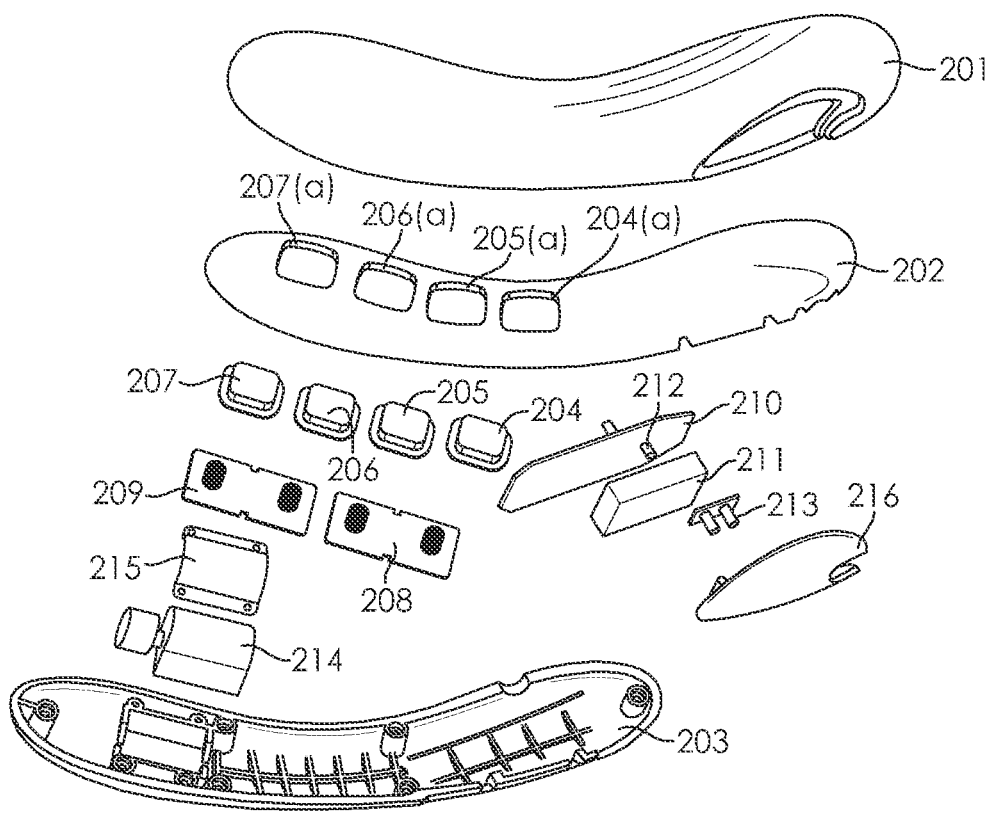
FIG. 2A is a first illustration of an exploded view of the sex toy with sensory feedback, in accordance with at least one embodiment of the present invention.

FIG. 2A is a first example exploded view of the sex toy with sensory feedback. The sex toy may be made up of a silicone case 201, a main body upper shell 202, and a main body lower shell 203. The main body upper shell 202 may include four holes 204(a), 205(a), 206(a), and 207(a) for the four trigger buttons 204, 205, 206, and 207. Under the four trigger buttons 204-207 may be two PCBs 208 and 209 (PCBs 208 and 209 may be combined into one PCB). Alternative embodiments may utilize materials other than silicone, and further, depending on the number and type of trigger buttons, the main body may be comprised of additional or fewer holes, suitable for the type of sensors being used.

In this preferred embodiment, the two PCBS 208 and 209 may be connected to the main PCB 210. On one side of the main PCB 210 may be a battery 211. The battery 211 may be rechargeable. On the other side of the main PCB 210 may be a light 212. Attached to the battery 211 may be a PCB with conductive needles 213. The battery 211 may be covered by a back cover 216.

In other embodiments, wherein the series of trigger buttons are partly in the main body upper shell and the main body lower shell (for example, some of the trigger buttons may be on the main body upper shell, the rest may be on the main body lower shell). The arrangement of the series of trigger buttons may be symmetrical or staggered (for example, symmetrical arrangement may mean that when the sex toy is thrusting into a woman or man's body, two buttons, one of which is in the main body upper shell and the other is in the main body lower shell may be triggered at the same time and stagger arrangement means when the sex toy is thrusting into a woman or man's body, all of those trigger buttons may be triggered one by one).

In this exemplary embodiment, the sex toy may include a motor 214. The motor 214 may be covered with a motor cover 215. The motor 214 may be connected to trigger buttons 204-207 via the PCBs 208 and 209. The motor 214 may turn on when at least one of the trigger buttons 204-207 are depressed.

Figure 2B:
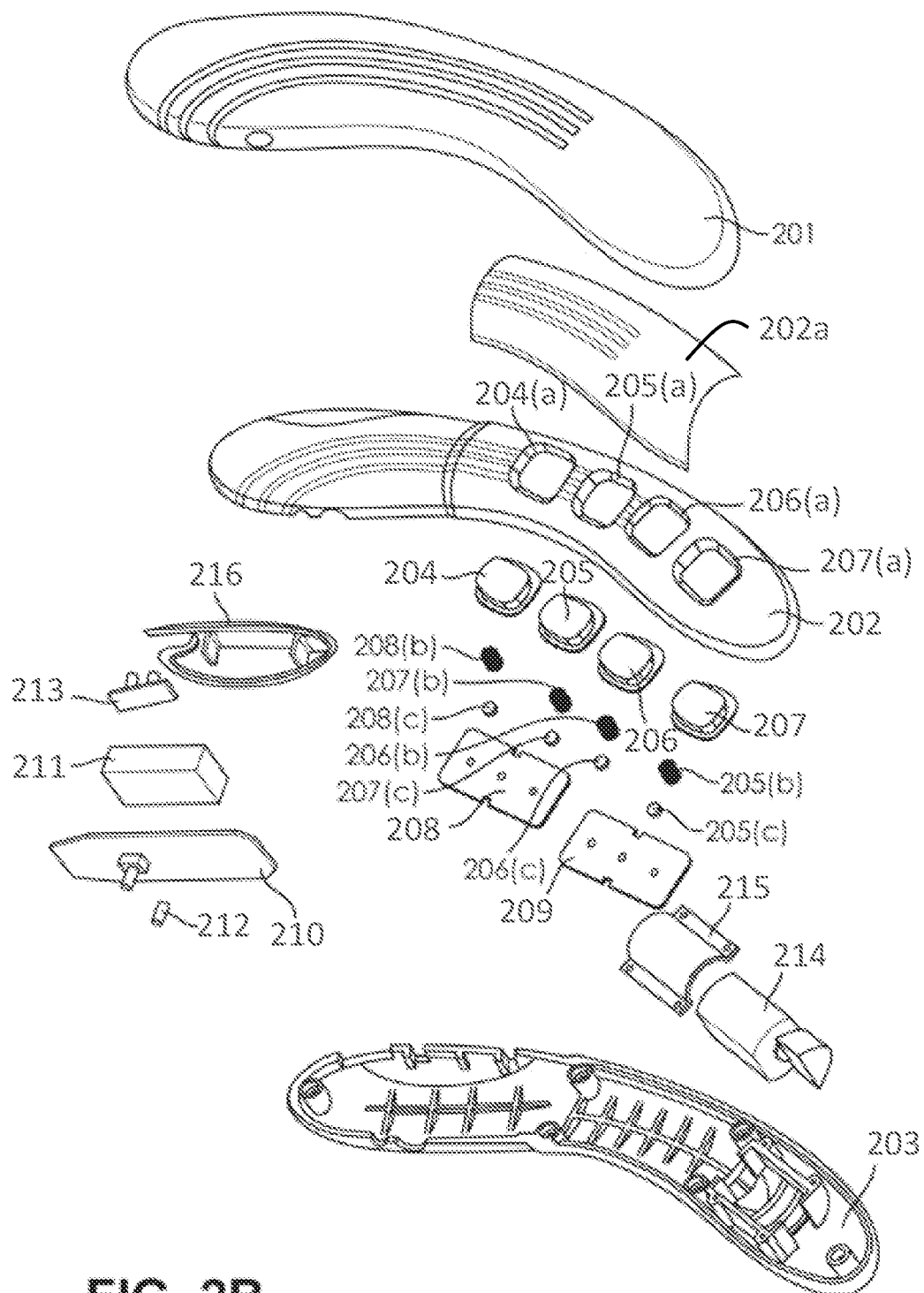
FIG. 2B is a second illustration of an exploded view of the sex toy with sensory feedback, in accordance with at least one embodiment of the present invention.

FIG. 2B is a second example exploded view of the sex toy with sensory feedback. In this embodiment, the sex toy may be made up of a silicone case 201, a silicone cushion 202a, a main body upper shell 202, a main body lower shell 203, and a back cover 216. The main body upper shell 202 may include four holes 204(a), 205(a) 206(a), and 207(a) for the four trigger buttons 204, 205, 206, and 207. Under each of the four trigger buttons 204-207 may be mechanical springs 205(b), 206(b), 207(b), and 208(b) and conductive foam plastics 205(c), 206(c), 207(c), and 208(c).

The sex toy may also include two printed circuit boards (PCBs) 208 and 209. These two PCBs 208 and 209 may be located under the trigger buttons 204-207. The two PCBS 208 and 209 may be connected to the main PCB 210. On one side of the main PCB 210 may be a battery 211. The battery 211 may be rechargeable. On the other side of the main PCB 210 may be a light 212. Attached to the battery 211 may be a PCB with conductive needles 213.

The sex toy may also include a motor 214. The motor 214 may be covered with a motor cover 215. The motor 214 may be connected to trigger buttons 204-207 via the PCBs 208 and 209. The motor 214 may turn on when at least one of the trigger buttons 204-207 are depressed.

Figure 3:
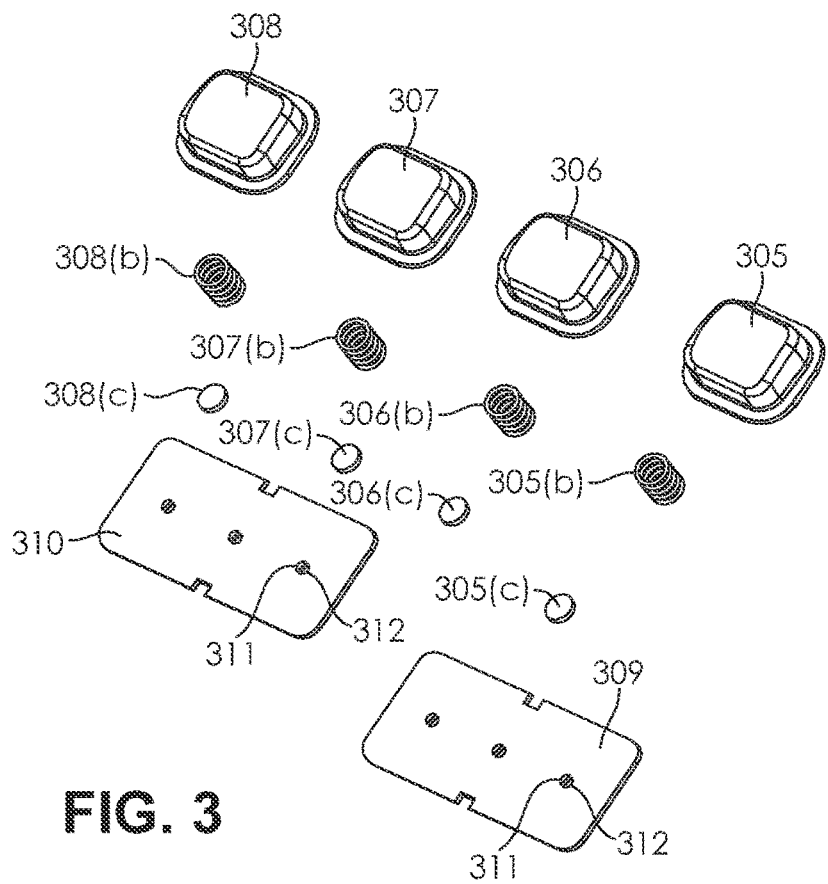
FIG. 3 is an illustration of an exploded view of a series of trigger buttons, in accordance with at least one embodiment of the present invention.

FIG. 3 is an example exploded view of the trigger buttons. The trigger buttons 305-308 may have mechanical springs 305(b)-308(b) underneath. The mechanical springs 305(b)-308(b) may have two ends, one connected to the trigger buttons 305-308 and one connected to conductive foam plastics 305(c)-308(c). There may be a gap between the conductive foam plastics 305(c)-308(c) and the PCBs 309 and 310. In a preferred embodiment, on a condition that the trigger buttons 305(a)-305(b) are depressed (e.g., via pressure from the user's vagina), the conductive foam plastics 305(c)-308(c) and the PCBs 309 and 310 make an electrical connection causing the motor (seen in FIG. 2 FIGS. 2A and 2B) to start.

The PCBs 309 and 310 may include conductive elements. The conductive elements may have two parts that are non-conductive 311 and 312. Once the trigger buttons 305(a)-308(a) are depressed (e.g., via pressure from the user's vagina), the conductive foam plastics 305(c)-308(c) and the PCBs 309 and 310 may be connected with each other, and in turn both non-conductive parts 311 and 312 may be covered by the conductive foam plastics 305(c)-308(c) to make an electrical connection.

The sex toy may be able to feel the pressure on different points, for example, at each of the four trigger points. The level of vibrations may react according the pressure, based on pre-defined settings. For example, the deeper the sex toy is inserted, activating more pressure points (or trigger points), the stronger the vibrations generated by the motor will be. Additionally or alternatively, the sex toy may be programmable by the user, such as via a controller or computing device (for example, a smart phone) connected to the sex toy via a wired or wireless connection.

The following chart is an example of the pressure levels felt by the sex toy:

and third trigger buttons may be engaged resulting in an even higher level of vibration (higher than that of level 2). When there is a pressure level of 4 on the sex toy, all four trigger buttons may be depressed. Therefore the conductive elements under all four trigger buttons may be engaged resulting in the highest level of vibration.

The interactive sex toy with sensory feedback described herein may send a signal to another person's sex toy based on the pressure sensors. The reactions of the other person's sex toy may react to the depth of insertion of the first sex toy. As illustrated in the following examples, the pressure at a first user's sex toy (female) may cause a reaction at a second user's sex toy (male) when used in tandem.

Figure 4:
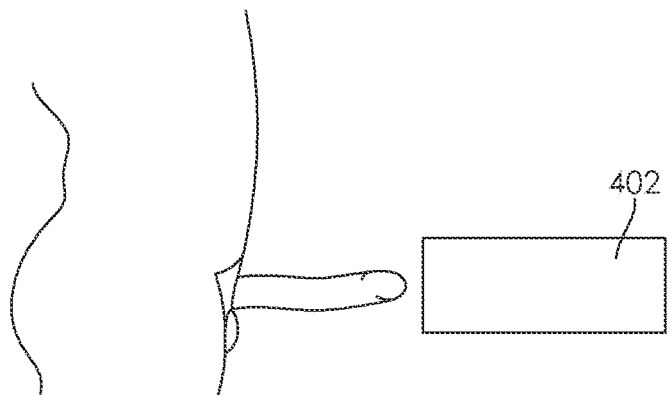
FIG. 4 is an example of the sex toy with no pressure exerted, in accordance with at least one embodiment of the present invention.
Figure 4:
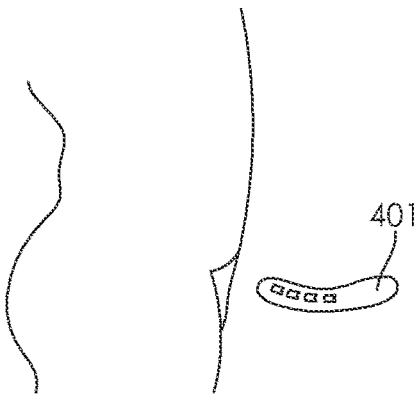

FIG. 4 is an example of the sex toy with no pressure exerted. In this exemplary embodiment, the sex toy 401 is not inserted into a user's vagina and feels no pressure. As a result the sex toy 401 does not cause a reaction at a second user's sex toy 402.

Figure 5:
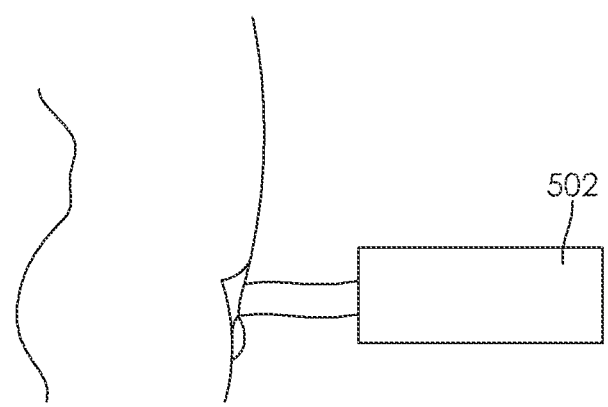
FIG. 5 is an example of the sex toy with a pressure level of 1 exerted, in accordance with at least one embodiment of the present invention.
Figure 5:
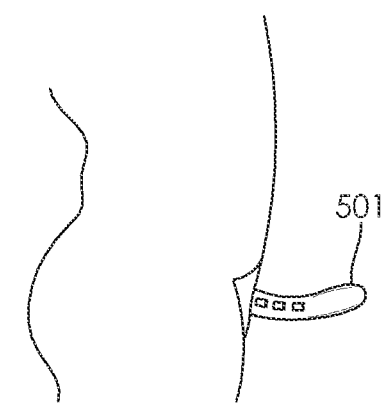

FIG. 5 is an example of the sex toy with a pressure level of 1 exerted. In this exemplary embodiment, the sex toy 501 is inserted into a user's vagina hitting the first trigger point. As a result the sex toy 501 causes a pressure reaction at a second user's sex toy 502.

Figure 6:
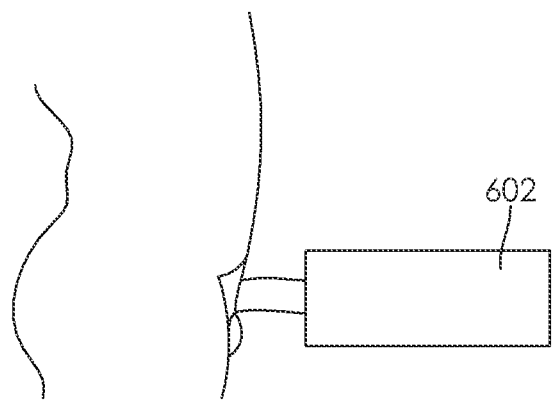
FIG. 6 is an example of the sex toy with a pressure level of 2 exerted, in accordance with at least one embodiment of the present invention.
Figure 6:
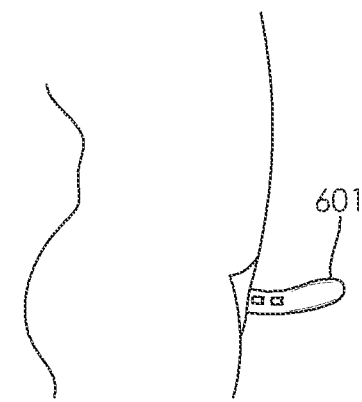

FIG. 6 is an example of the sex toy with a pressure level of 2 exerted. In the exemplary embodiment, the sex toy 601 is inserted into a user's vagina hitting the first and second trigger points. As a result the sex toy 601 causes a pressure reaction at the second user's sex toy 602. For instance, the level 2 pressure reaction at the second user's sex toy 602 may be greater than the level 1 pressure reaction.

Figure 7:
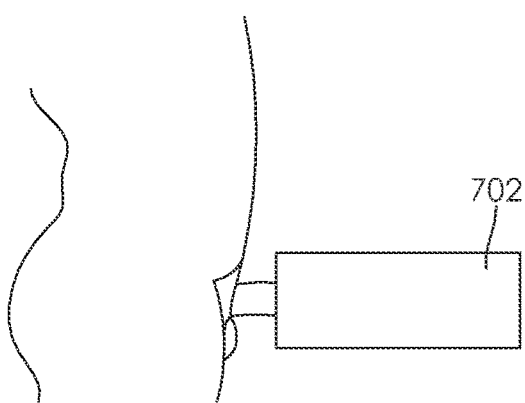
FIG. 7 is an example of the sex toy with a pressure level of 3 exerted, in accordance with at least one embodiment of the present invention.
Figure 7:
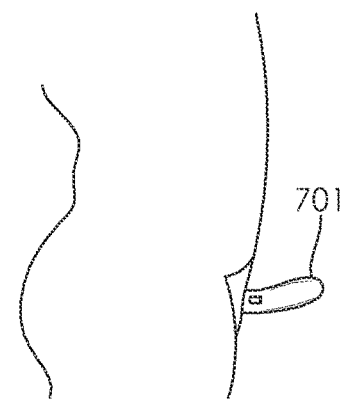

FIG. 7 is an example of the sex toy with a pressure level of 3 exerted. In the exemplary embodiment, the sex toy 701 is inserted into a user's vagina hitting the first, second, and third trigger points. As a result the sex toy 701 causes a pressure reaction at the second user's sex toy 702. For instance, the level 3 pressure reaction at the second user's sex toy 702 may be greater than the level 2 pressure reaction.

Figure 8:
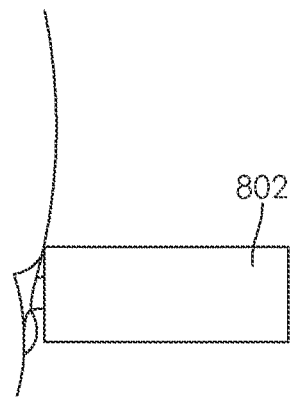
FIG. 8 is an example of the sex toy with a pressure level of 4 exerted, in accordance with at least one embodiment of the present invention.
Figure 8:

FIG. 8 is an example of the sex toy with a pressure level of 4 exerted. In the exemplary embodiment, the sex toy 801 is inserted into a user's vagina hitting all four of the trigger points. As a result the sex toy 801 causes a pressure reaction at the second user's sex toy 802. For instance, the level 4

| Trigger button 1 | Trigger button 2 | Trigger button 3 | Trigger button 4 | Pressure level |
| --- | --- | --- | --- | --- |
| Non-conduction | Non-conduction | Non-conduction | Non-conduction | No pressure |
| Conduction | Non-conduction | Non-conduction | Non-conduction | Level 1 |
| Conduction | Conduction | Non-conduction | Non-conduction | Level 2 |
| Conduction | Conduction | Conduction | Non-conduction | Level 3 |
| Conduction | Conduction | Conduction | Conduction | Level 4 |

When there is no pressure exerted on the sex toy, none of the trigger buttons may be depressed, and the two parts of the conductive element may be non-conductive 311 and 312, so that the conductive element on the PCBs are non-conductive. When there is a pressure level of 1 on the sex toy, only the first trigger button may be depressed. Therefore only the conductive element under the first trigger button may be engaged resulting in a lower level of vibration. When there is a pressure level of 2 on the sex toy, both the first and second trigger buttons may be depressed. Therefore the conductive elements under the first and second trigger button may be engaged resulting in a higher level of vibration. When there is a pressure level of 3 on the sex toy, the first, second, and third trigger buttons may be depressed. Therefore the conductive elements under the first, second, pressure reaction at the second user's sex toy 802 may be greater than the level 3 pressure reaction.

There are multiple ways for the interactive sex toy with sensory feedback to communicate with a second user. A first user's sex toy may transmit signals to a second user's sex toy to react in response to the first user's masturbation. In response the second user's sex toy may transmit signals to the first user's sex toy to react to the second user's masturbation.

In a first example, the sex toy may send a signal to another user's sex toy via a smart phone or other computing device (e.g., laptop, tablet PC, wearable computing apparatus). One of ordinary skill in the art would appreciate that there are numerous types of computing devices that could be used with embodiments of the present invention, and embodiments of the present invention are contemplated for use with any appropriate computing device.

Figure 9:
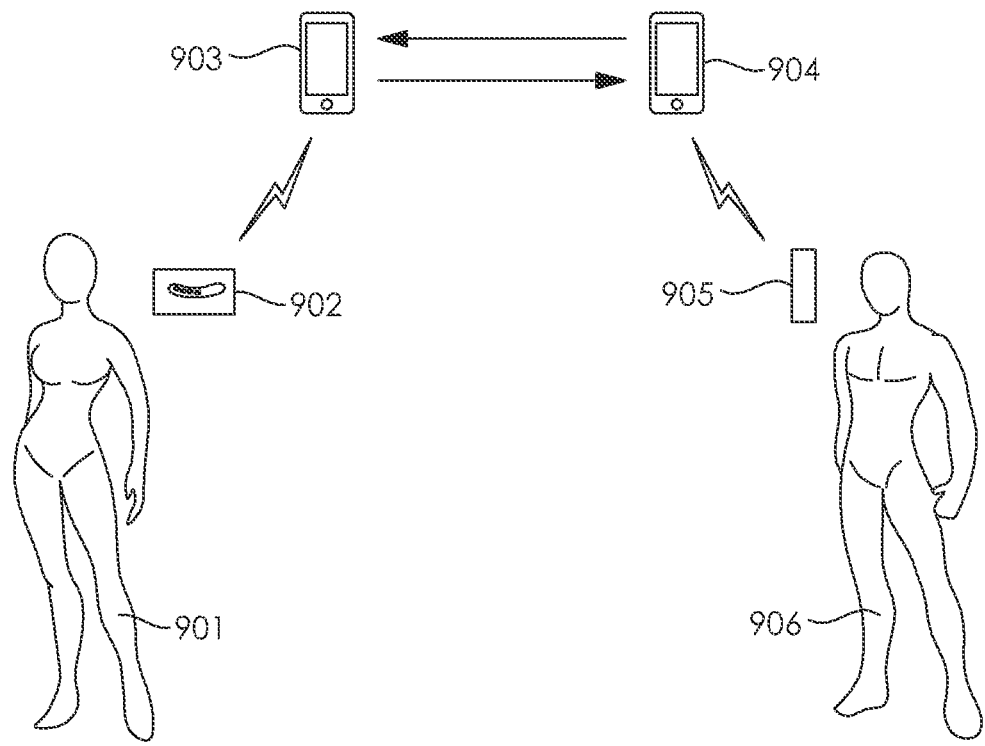
FIG. 9 is an example of two users' sex toys communicating via smart phones to activate their respective sex toys, in accordance with at least one embodiment of the present invention.

FIG. 9 is an example of two users' sex toys communicating via cell phones to activate their respective sex toys. A first user 901 (female) may utilize a first sex toy 902. When the first sex toy 902 is inserted into the first user's vagina, the pressure sensors may react to the applied pressure and send a signal to the first user's cell phone 903. The data may then be transmitted to a second user's cell phone 904. The second user's sex toy 905 may receive a signal from the second user's cell phone 904 and react on the second user (male) 906 in response to the first user's 901 applied pressure. Additionally, the signals may transmit from both the first user's sex toy to the second user's sex toy and vice versa.

Figure 10:
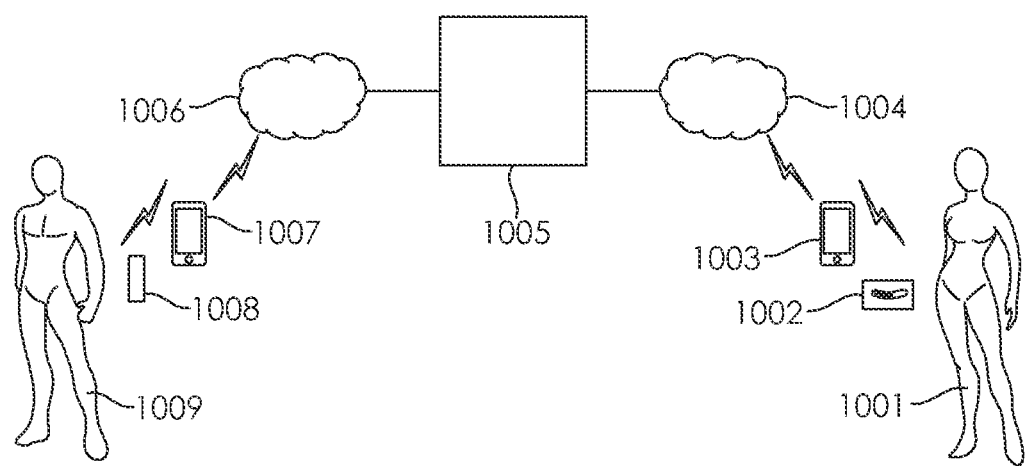
FIG. 10 is an example of two users' sex toys communicating via the internet, in accordance with at least one embodiment of the present invention.

In a second example, the sex toy may send a signal to another user's sex toy via the internet, for example, a dating system or the like. FIG. 10 is an example of two users' sex toys communicating via the internet. A first user 1001 (female) may utilize a first sex toy 1002. For example, when the first sex toy 1002 is inserted into the first user's vagina, the pressure sensors may react to the applied pressure and transmit a signal to the first user's cell phone 1003. The first user's cell phone 1003 may transmit the received signal to the network 1004. The network 1004 may transmit the received signal to the internet 1005. The internet 1005 may transmit the received signal to the second user's network 1006. The second user's network 1006 may transmit the received signal to the second user's cell phone 1007. The second user's sex toy 1008 may receive the signal from the second user's cell phone 1007 and react on the second user 1009 (male) in response to the first user's 1001 applied pressure. Additionally, the signals may transmit from both the first user's sex toy to the second user's sex toy and vice versa.

Figure 11:
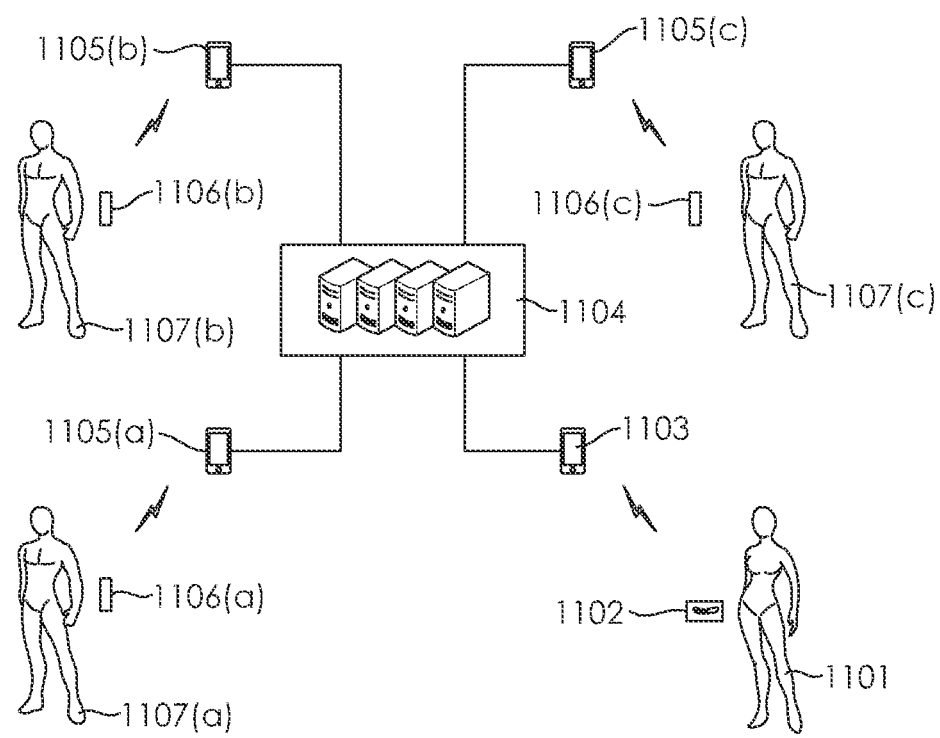
FIG. 11 is an example of several users' sex toys communicating via the internet, in accordance with at least one embodiment of the present invention.

In a third example, the sex toy may send a signal to several other users' sex toys via the internet, for example, to a cloud server with a broadcast platform. FIG. 11 is an example of several users' sex toys communicating via the internet. A first user 1101 (female, for example a model in a broadcast platform) may utilize a first sex toy 1102. When the first sex toy 1102 is inserted into the first user's vagina (or other cavity), the pressure sensors may react to the applied pressure and transmit a signal to the first user's cell phone 1103. The first user's cell phone 1103 may transmit the received signal to a cloud server 1104. The cloud server 1104 may distribute the signal to several other users or store the data for a later use. The cloud server 1104 may transmit the received signal to the other user's cell phones 1105(a), 1105(b), and 1105(c). The other user's sex toys 1106(a), 1106(b), and 1106(c) may receive the signal from the other user's cell phones 1105(a), 1105(b), and 1105(c) and react on the other users 1107(a), 1107(b), and 1107(c) (male) in response to the first user's 1101 applied pressure. Additionally, the signals may transmit from both the first user's sex toy to the other users' sex toys and vice versa.

Figure 12:
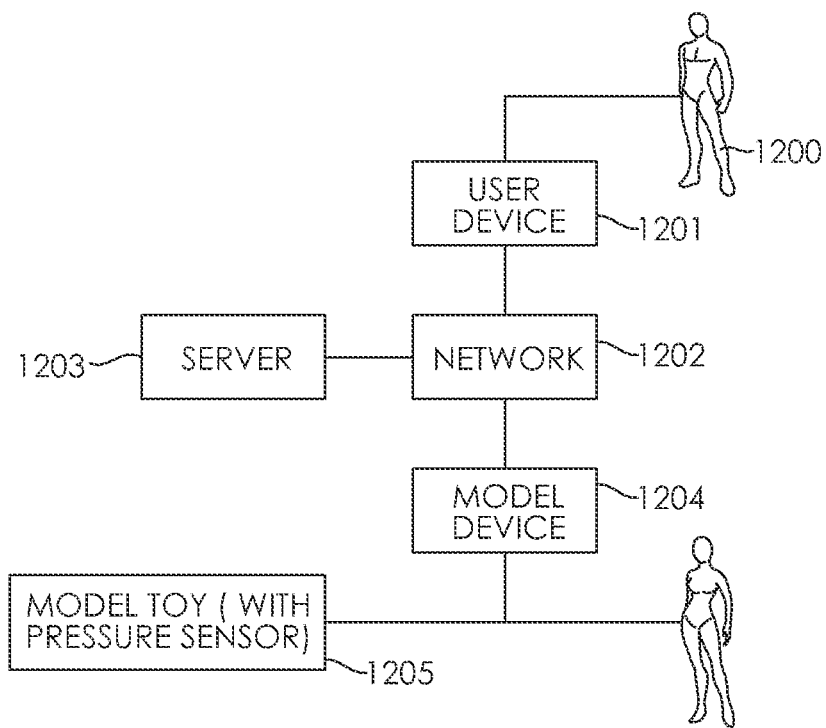
FIG. 12 is a first exemplary method for using the interactive sex toy with sensory feedback.

FIG. 12 is a first exemplary method for using the interactive sex toy with sensory feedback. A first user 1200 may transmit a signal via device 1201. The signal may be received at the network 1202 and may either be stored on a server 1203 or transmitted to a second user's device 1204. The second user's device 1204 may transmit the signal to the sex toy 1205, causing the sex toy 1205 to react to the input from the first user 1201.

Figure 13:
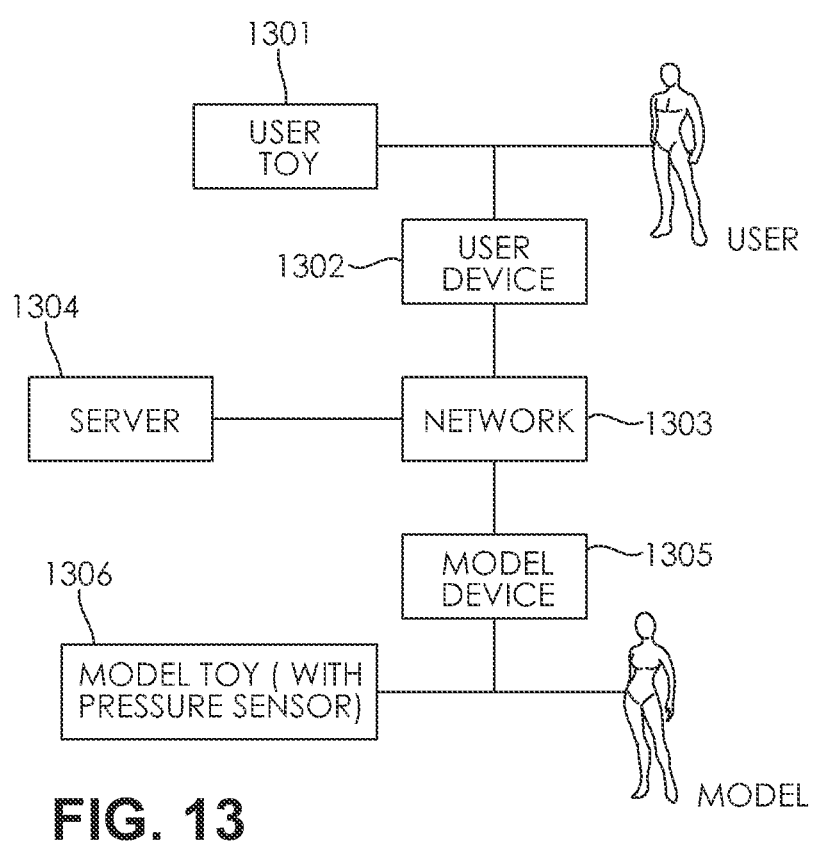
FIG. 13 is a second exemplary method for using the interactive sex toy with sensory feedback.

FIG. 13 is a second exemplary method for using the interactive sex toy with sensory feedback. A first user's sex toy 1301 may transmit a signal to a first user's device 1302. The signal may be received at the network 1303 and may either be stored on a server 1304 or transmitted to a second user's device 1305. The second user's device 1305 may transmit the signal to the second user's sex toy 1306, causing the sex toy 1305 to react to the first user's sex toy 1301. Additionally, the signals may transmit from both the first user's sex toy to the other users' sex toys and vice versa.

As described herein, the interactive sex toy with sensory feedback may be used via the internet.

Further, while many of the examples given herein describe interaction between a female using a first sex toy and a male using a second sex toy, embodiments of the present invention are contemplated for any combination of user type and gender. For instance, two female users could participate in a manner where a first sex toy acts as controller and provides pressure level information to a second sex toy inserted into a cavity of the second user. One of ordinary skill in the art would appreciate that there are numerous combination that could be accomplished through use of the apparatus and methods detailed herein.

Figure 14:
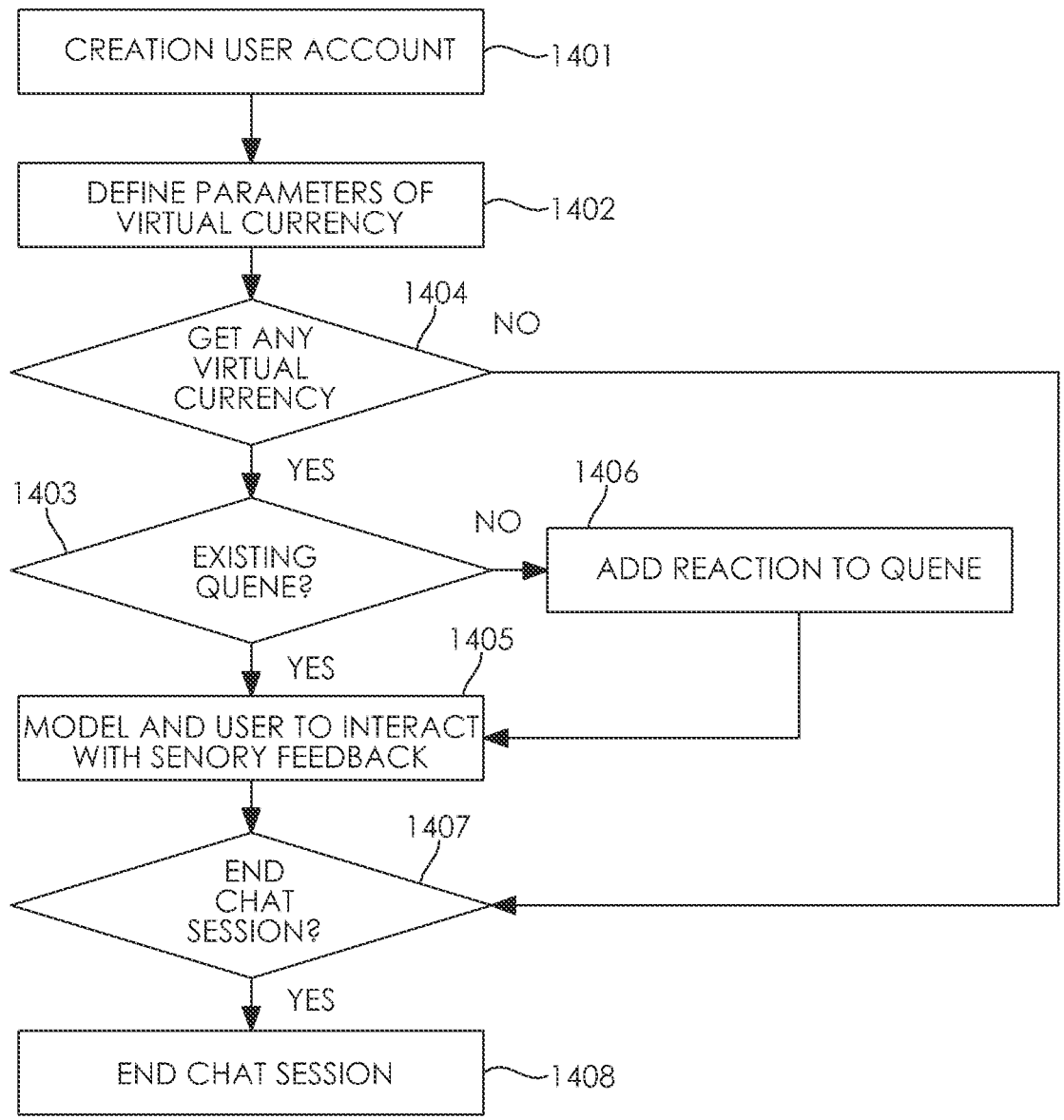
FIG. 14 is a flow chart for engaging in a sexual encounter using the sex toy with sensory feedback with a payment system, in accordance with at least one embodiment of the present invention.

FIG. 14 is a flow chart for engaging in a sexual encounter using the sex toy with sensory feedback with a payment system. A user may first create an account 1401. Once the user creates an account, they may define the parameters of virtual currency 1402, for example, how much services cost and what kind of currency is accepted. If the user does not have the required virtual currency 1404, then the user's session ends 1408.

If the user has the required virtual currency 1403, a determination may be made if there is an existing queue of user's reactions. If there is not an existing queue 1406, the reaction is added to a queue. If this is an existing queue 1405, then the user and another user interact using the sex toy with sensory feedback. Once the users have finished their session 1407, the chat session may end 1408.

Figure 15:
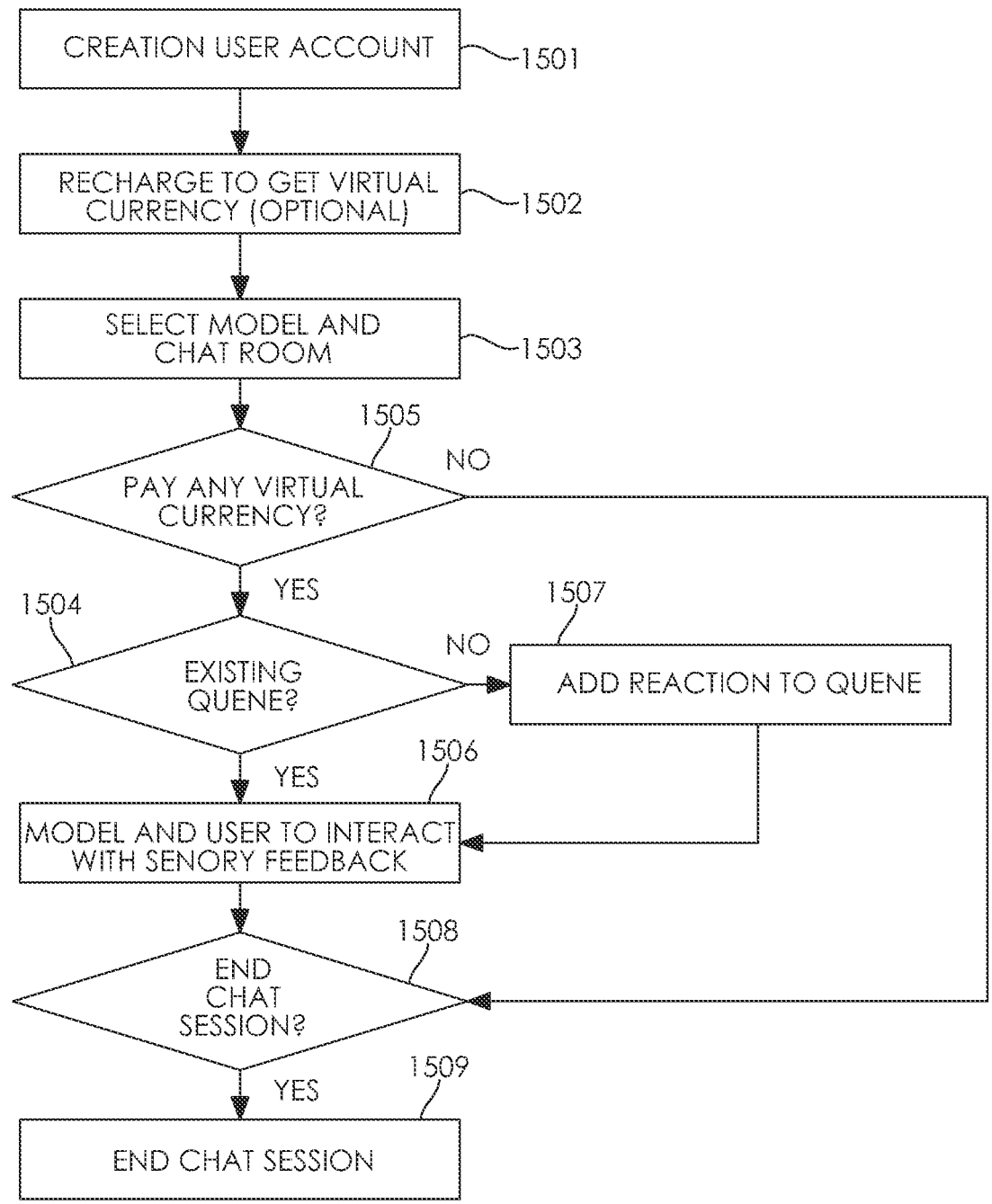
FIG. 15 is a flow chart for engaging in a sexual encounter using the sex toy with sensory feedback with a payment system, in accordance with at least one embodiment of the present invention.

FIG. 15 is a flow chart for engaging in a sexual encounter using the sex toy with sensory feedback with a payment system. A user may first create an account 1501. Once the user creates an account, the user may recharge to get virtual currency 1502. The user may then select a chat room 1503. Once the user selects a chat room, the user may either may a virtual currency payment 1504 or not 1505. If the user does not make a virtual currency payment 1505, then the user's session ends 1509.

If the user does make a virtual currency payment 1504, a determination may be made if there is an existing queue of user's reactions. If there is not an existing queue 1507, the reaction is added to a queue. If this is an existing queue 1506, then the user and another user interact using the sex toy with sensory feedback. Once the users have finished their session 1508, the chat session may end 1509.

Figure 16:
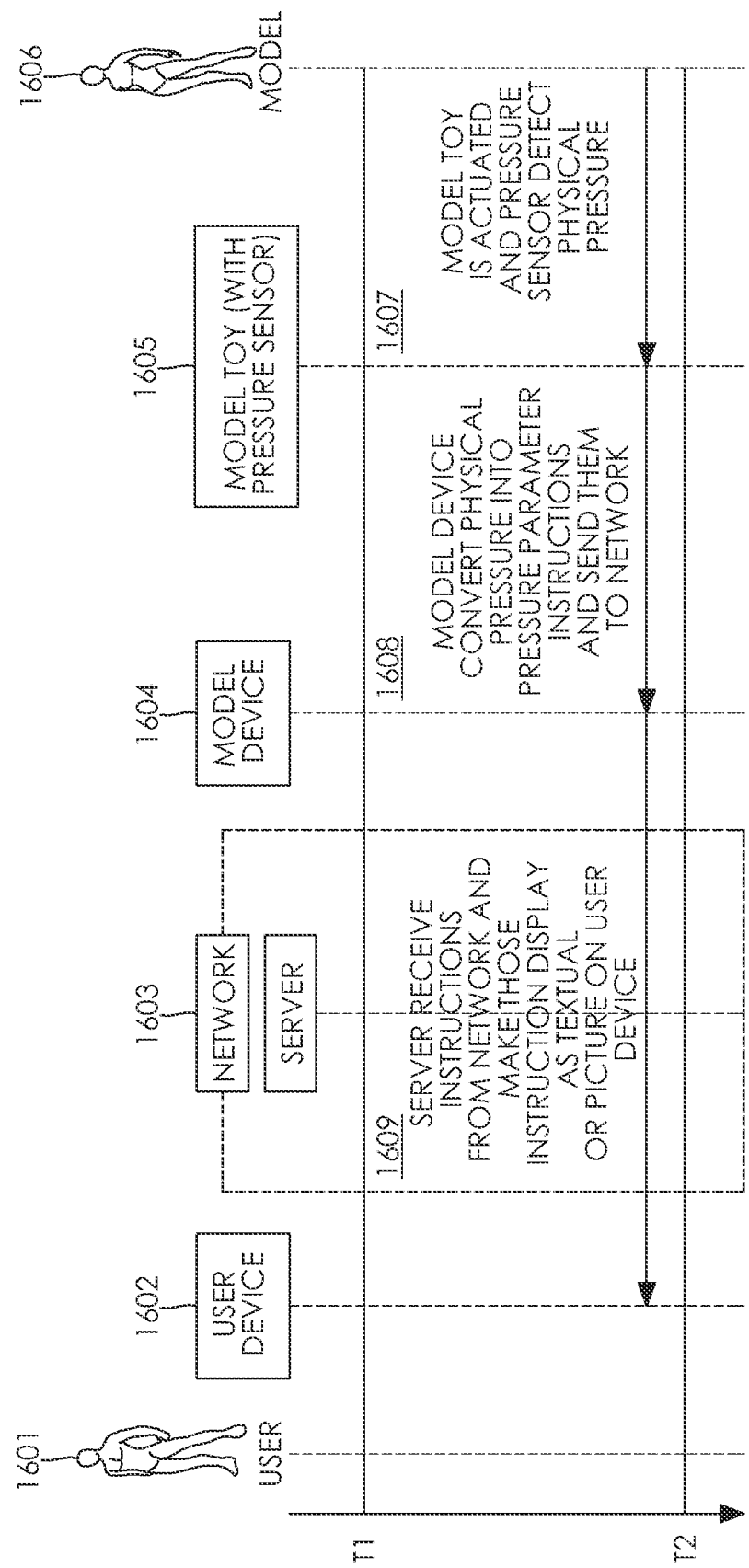
FIG. 16 is an exemplary flow chart where only one user has a sex toy, in accordance with at least one embodiment of the present invention.

FIG. 16 is an example flow chart where only one user has a sex toy. The flow chart may include a first user 1601, a first user device 1602, for example, a cell phone, a network/server 1603, a second user 1606, a sex toy 1605, and a second user device 1604. The second user 1606 may actuate the sex toy 1605. The pressure sensors of the sex toy 1605 may detect the physical pressure 1607 and transmit these pressures to the second user's device 1604. The second user's device 1604 may convert the physical pressure into pressure parameter instructions and transmit 1608 the instructions to the network/server 1603. The network/server 1603 may receive the instructions, convert them to text or pictures, and transmit them to the first user's device 1602.

Figure 17:
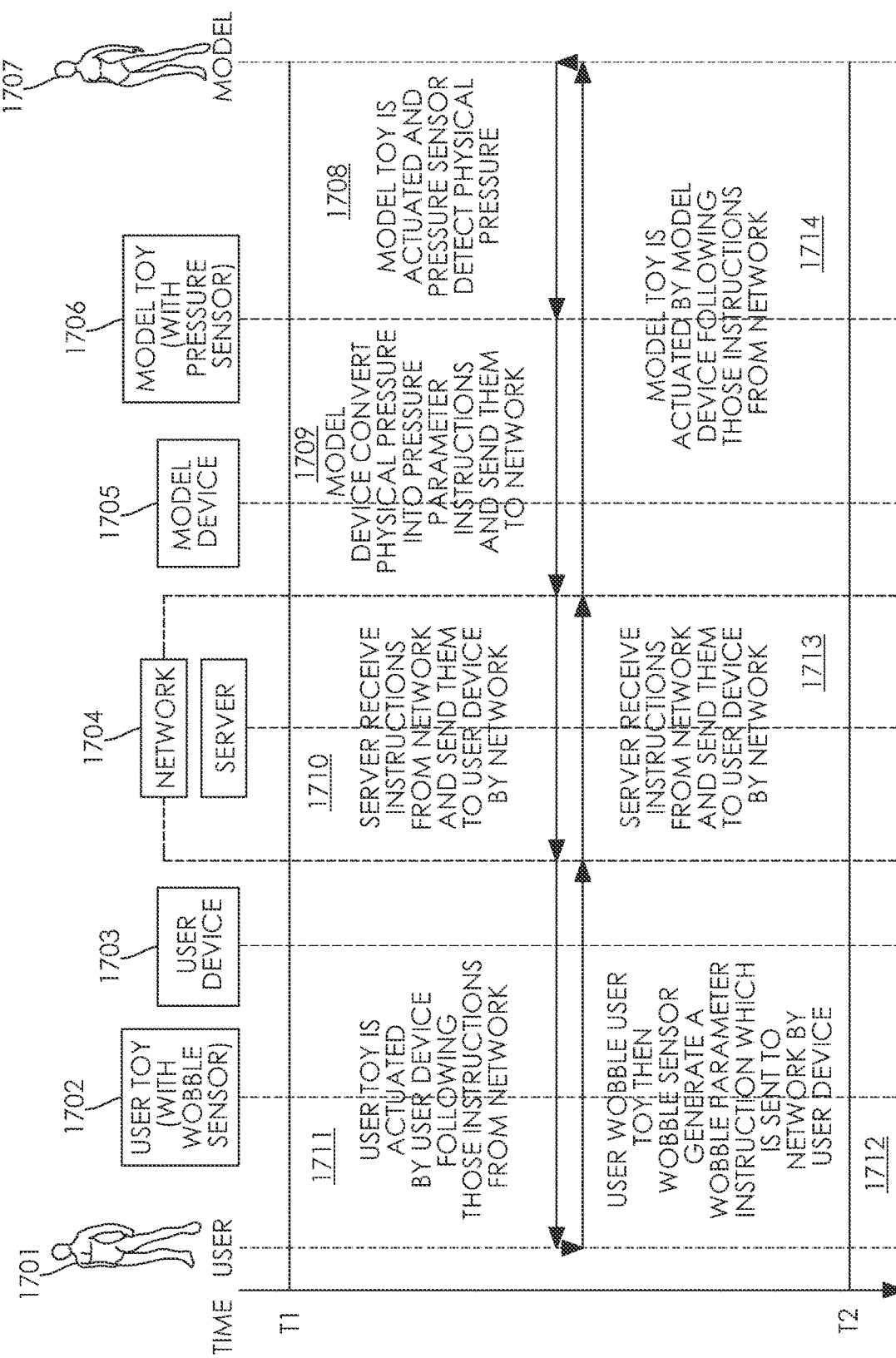
FIG. 17 is an exemplary flow chart where both users have a sex toy, in accordance with at least one embodiment of the present invention.

FIG. 17 is an example flow chart where both users have a sex toy. The chart may include a first user 1071, a first sex toy 1702, a first user device 1703, a network/server 1704, a second user 1707, a second sex toy 1706, and a second user device 1705. The second user 1707 may actuate the sex toy 1706. The pressure sensors of the sex toy 1706 may detect physical pressure 1708 and transmit these pressures to the second user's device 1705. The second user's device 1705 may convert the physical pressure into pressure parameter instructions and transmit 1709 the instruction to the network/server 1704. The network/server 1704 may receive the instructions and transmit them 1710 to the first user's device 1703. The first sex toy 1702 may be actuated by the first user device 1703 and follow the instructions 1711 from the network/server 1704.

The first user sex toy 1702 may generate wobble parameters and transmit these parameters to the first user's device 1703. The first user device 1703 may then transmit 1712 these parameters to the network/server 1704. The network/server 1704 may receive the parameters and transmit them 1713 to the second user device 1705. The second sex toy 1706 may be actuated by the second user device 1705 and follow the instructions 1714 from the network/server 1704.

Figure 18:
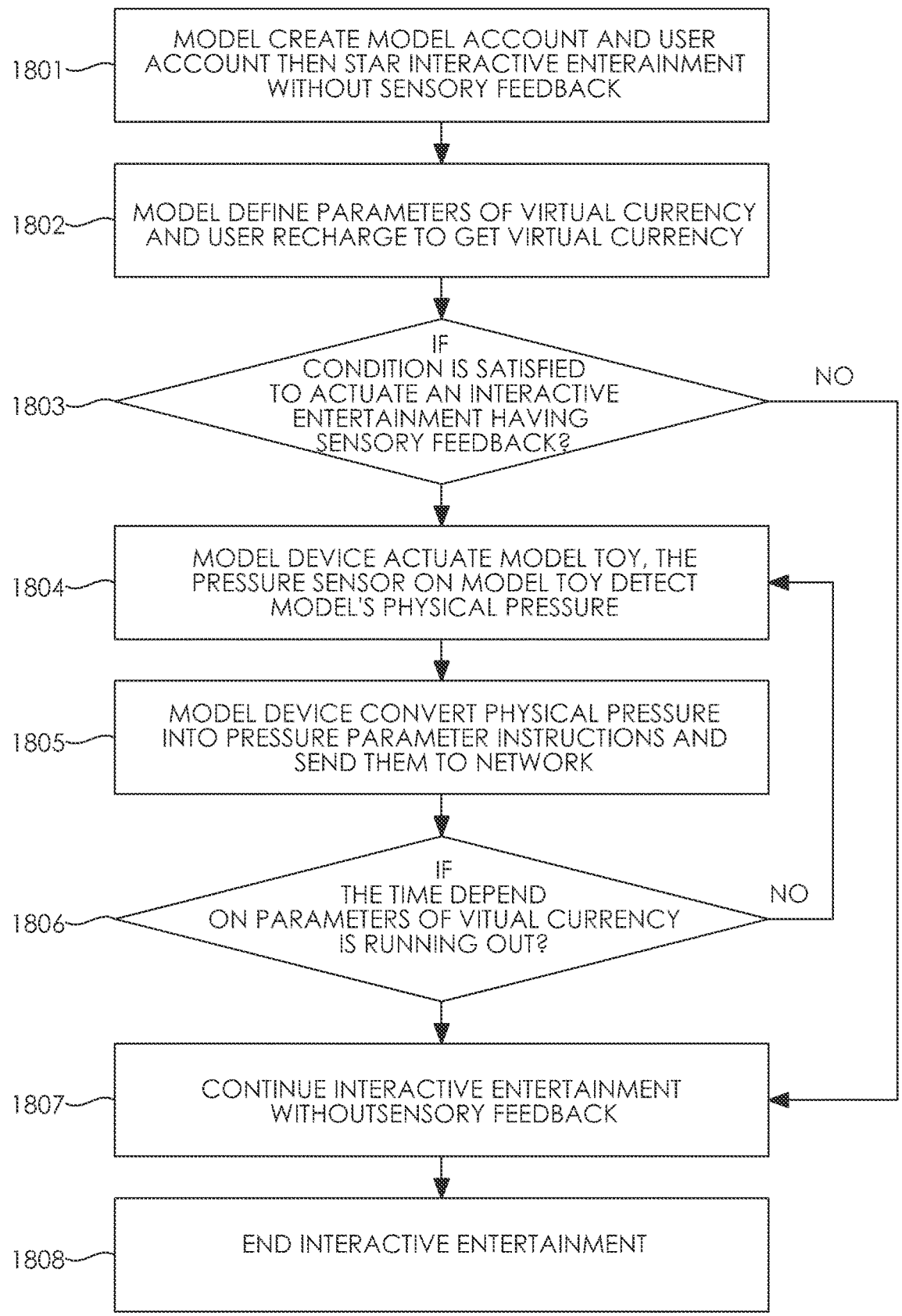
FIG. 18 is an exemplary flow chart of communication between a first and second user, in accordance with at least one embodiment of the present invention.

FIG. 18 is an example flow chart of communication between a first and second user. A first and second user may create accounts and begin interactive entertainment without sensory feedback 1801. The first user may define parameters of virtual currency and the second user may recharge to get virtual currency 1802. On a condition that actuating interactive entertainment with sensory feedback is satisfied 1803 (for example, in a broadcast platform scenario, if a user transmits a certain amount of tips to a model, then the condition of actuating interactive entertainment with sensory feedback is satisfied), a first user's device may actuate a first user's sex toy and the pressure sensors on the sex toy may detect physical pressure 1804. The first user's device may convert the physical pressure into pressure parameters instructions and transmit them to the network 1805. A second user's device may get the pressure parameters instructions from the network and transmit them to a second user's sex toy to actuate the second user's sex toy based on the received pressure parameter instructions. On a condition that the virtual currency is not running out 1806, the pressure sensor on the first user's sex toy may continue to detect physical pressure 1804 and convert the physical pressure into pressure parameters instructions and transmit them to the network 1805. On a condition that the virtual currency is running out 1806, the first and second user may continue entertainment without sensory feedback 1807 and the interactive entertainment may end 1808.

On a condition that actuating interactive entertainment sensory feedback is not satisfied 1803, the first and second user may continue entertainment without sensory feedback 1807 and the interactive entertainment may end 1808.

The communications means of the system may be any means for communicating data, including image and video, over one or more networks or to one or more peripheral devices attached to the system, or to a system module or component. Appropriate communications means may include, but are not limited to, wireless connections, wired connections, cellular connections, data port connections, Bluetooth® connections, near field communications (NFC) connections, or any combination thereof. One of ordinary skill in the art will appreciate that there are numerous communications means that may be utilized with embodiments of the present disclosure, and embodiments of the present disclosure are contemplated for use with any communications means.

Traditionally, a computer program includes a finite sequence of computational instructions or program instructions. It will be appreciated that a programmable apparatus or computing device can receive such a computer program and, by processing the computational instructions thereof, produce a technical effect.

A programmable apparatus or computing device includes one or more microprocessors, microcontrollers, embedded microcontrollers, programmable digital signal processors, programmable devices, programmable gate arrays, programmable array logic, memory devices, application specific integrated circuits, or the like, which can be suitably employed or configured to process computer program instructions, execute computer logic, store computer data, and so on. Throughout this disclosure and elsewhere a computing device can include any and all suitable combinations of at least one general purpose computer, special-purpose computer, programmable data processing apparatus, processor, processor architecture, and so on. It will be understood that a computing device can include a computer-readable storage medium and that this medium may be internal or external, removable and replaceable, or fixed. It will also be understood that a computing device can include a Basic Input/Output System (BIOS), firmware, an operating system, a database, or the like that can include, interface with, or support the software and hardware described herein.

Embodiments of the system as described herein are not limited to applications involving conventional computer programs or programmable apparatuses that run them. It is contemplated, for example, that embodiments of the disclosure as claimed herein could include an optical computer, quantum computer, analog computer, or the like.

Regardless of the type of computer program or computing device involved, a computer program can be loaded onto a computing device to produce a particular machine that can perform any and all of the depicted functions. This particular machine (or networked configuration thereof) provides a technique for carrying out any and all of the depicted functions.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. Illustrative examples of the computer readable storage medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A data store may be comprised of one or more of a database, file storage system, relational data storage system or any other data system or structure configured to store data. The data store may be a relational database, working in conjunction with a relational database management system (RDBMS) for receiving, processing and storing data. A data store may comprise one or more databases for storing information related to the processing of moving information and estimate information as well one or more databases configured for storage and retrieval of moving information and estimate information.

Computer program instructions can be stored in a computer-readable memory capable of directing a computer or other programmable data processing apparatus to function in a particular manner. The instructions stored in the computer-readable memory constitute an article of manufacture including computer-readable instructions for implementing any and all of the depicted functions.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

The elements depicted in flowchart illustrations and block diagrams throughout the figures imply logical boundaries between the elements. However, according to software or hardware engineering practices, the depicted elements and the functions thereof may be implemented as parts of a monolithic software structure, as standalone software components or modules, or as components or modules that employ external routines, code, services, and so forth, or any combination of these. All such implementations are within the scope of the present disclosure. In view of the foregoing, it will be appreciated that elements of the block diagrams and flowchart illustrations support combinations of means for performing the specified functions, combinations of steps for performing the specified functions, program instruction technique for performing the specified functions, and so on.

It will be appreciated that computer program instructions may include computer executable code. A variety of languages for expressing computer program instructions are possible, including without limitation C, C++, Java, JavaScript, assembly language, Lisp, HTML, Perl, and so on. Such languages may include assembly languages, hardware description languages, database programming languages, functional programming languages, imperative programming languages, and so on. In some embodiments, computer program instructions can be stored, compiled, or interpreted to run on a computing device, a programmable data processing apparatus, a heterogeneous combination of processors or processor architectures, and so on. Without limitation, embodiments of the system as described herein can take the form of web-based computer software, which includes client/server software, software-as-a-service, peer-to-peer software, or the like.

In some embodiments, a computing device enables execution of computer program instructions including multiple programs or threads. The multiple programs or threads may be processed more or less simultaneously to enhance utilization of the processor and to facilitate substantially simultaneous functions. By way of implementation, any and all methods, program codes, program instructions, and the like described herein may be implemented in one or more thread. The thread can spawn other threads, which can themselves have assigned priorities associated with them. In some embodiments, a computing device can process these threads based on priority or any other order based on instructions provided in the program code.

Unless explicitly stated or otherwise clear from the context, the verbs "process" and "execute" are used interchangeably to indicate execute, process, interpret, compile, assemble, link, load, any and all combinations of the foregoing, or the like. Therefore, embodiments that process computer program instructions, computer-executable code, or the like can suitably act upon the instructions or code in any and all of the ways just described.

The functions and operations presented herein are not inherently related to any particular computing device or other apparatus. Various general-purpose systems may also be used with programs in accordance with the teachings herein, or it may prove convenient to construct more specialized apparatus to perform the required method steps. The required structure for a variety of these systems will be apparent to those of ordinary skill in the art, along with equivalent variations. In addition, embodiments of the disclosure are not described with reference to any particular programming language. It is appreciated that a variety of programming languages may be used to implement the present teachings as described herein, and any references to specific languages are provided for disclosure of enablement and best mode of embodiments of the disclosure. Embodiments of the disclosure are well suited to a wide variety of computer network systems over numerous topologies. Within this field, the configuration and management of large networks include storage devices and computing devices that are communicatively coupled to dissimilar computing and storage devices over a network, such as the Internet, also referred to as "web" or "world wide web".

Throughout this disclosure and elsewhere, block diagrams and flowchart illustrations depict methods, apparatuses (e.g., systems), and computer program products. Each element of the block diagrams and flowchart illustrations, as well as each respective combination of elements in the block diagrams and flowchart illustrations, illustrates a function of the methods, apparatuses, and computer program products. Any and all such functions ("depicted functions") can be implemented by computer program instructions; by special-purpose, hardware-based computer systems; by combinations of special purpose hardware and computer instructions; by combinations of general purpose hardware and computer instructions; and so on—any and all of which may be generally referred to herein as a "component", "module," or "system."

While the foregoing drawings and description set forth functional aspects of the disclosed systems, no particular arrangement of software for implementing these functional aspects should be inferred from these descriptions unless explicitly stated or otherwise clear from the context.

Each element in flowchart illustrations may depict a step, or group of steps, of a computer-implemented method. Further, each step may contain one or more sub-steps. For the purpose of illustration, these steps (as well as any and all other steps identified and described above) are presented in order. It will be understood that an embodiment can contain an alternate order of the steps adapted to a particular application of a technique disclosed herein. All such variations and modifications are intended to fall within the scope of this disclosure. The depiction and description of steps in any particular order is not intended to exclude embodiments having the steps in a different order, unless required by a particular application, explicitly stated, or otherwise clear from the context.

The functions, systems and methods herein described could be utilized and presented in a multitude of languages. Individual systems may be presented in one or more languages and the language may be changed with ease at any point in the process or methods described above. One of ordinary skill in the art would appreciate that there are numerous languages the system could be provided in, and embodiments of the present disclosure are contemplated for use with any language.

It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments.

It will be apparent to those skilled in the art that various modifications and variations can be made to the disclosed system and method. Other embodiments will be apparent to those skilled in the art from consideration of the specification and practice of the disclosed method and apparatus. It is intended that the specification and examples be considered as exemplary only, with a true scope being indicated by the following claims.

What is claimed:

1. A system, comprising:
   a memory device having stored thereon a set of instructions; and
   a processor configured to execute said set of instructions to:
      establish a communication between a first user's device and a second user's device;
      wherein the first user's device is configured to broadcast a live video through a broadcast platform and the second user's device is configured to receive the live video through the broadcast platform;
      predefine one or more preset parameters using the first user's device;
      determine whether one or more input parameters satisfies the one or more preset parameters, in response to the first user's device receiving the one or more input parameters from the second user's device, wherein when the one or more input parameters satisfies the one or more preset parameters, communicate, using a first sex toy, sensing data to the first user's device when the first sex toy is manipulated by a first user, wherein the sensing data is detected by at least one sensor integrated with the first sex toy;
      wherein the first sex toy is configured to communicate with the first user's device, and be actuated by the first user's device or to be manipulated by the first user;
      transmit, by the first user's device, the sensing data to the second user's device;
      receive, by the second user's device, the sensing data from the first user's device; and
      actuate, by the second user's device, a second sex toy according to the sensing data as an interactive feedback, such that the second sex toy reacts to the manipulation of the first sex toy in real-time or in near real-time;
      wherein the second sex toy is configured to communicate with the second user's device, and be actuated by the second user's device or to be manipulated by a second user; and
      wherein determining whether the one or more input parameters satisfies the one or more preset parameters includes establishing the communication in response to a certain amount of tips being transmitted from the first user's device to the second user's device, or from the second user's device to the first user's device.

2. The system of claim 1, wherein:
   the sensing data includes at least one selected from the group of tactile data, pressure data, wobble data, temperature data, inserting depth data, and combinations thereof, the sensing data being sensed by the at least one sensor.

3. The system of claim 2, wherein the first sex toy or the second sex toy includes a female sex toy or a male sex toy, and manipulating the first sex toy or the second sex toy includes:
   inserting the female sex toy into a body part of the user or inserting a body part of the user into the male sex toy; and
   actuating the first sex toy or the second sex toy includes actuating the sex toy to perform at least one selected from the group of vibration, rotation, swinging, inhalation, temperature variation, contraction, reciprocation, and combinations thereof.

4. The system of claim 2, wherein detecting the sensing data with the at least one sensor of the first sex toy includes determining a depth to which the first sex toy is inserted in a user's body, or to which a genital organ of the user's body is received in the first sex toy.

5. The system of claim 2, wherein actuating the second sex toy according to the sensing data as an interactive feedback includes:
   based on a magnitude of the sensing data, actuating the second sex toy dynamically at different levels.

6. The system of claim 5, wherein based on the magnitude of the sensing data, actuating the second sex toy dynamically at different levels includes at least one selected from the group of:
   as a magnitude of the pressure data or the wobble data increases, the more intensively the second sex toy is actuated;
   as a magnitude of the temperature data increases, a temperature of the second sex toy increases; and
   combinations thereof.

7. The system of claim 1, wherein establishing the communication between the first user device and the second user device includes establishing the communication through the broadcast platform or a one-to-one chat session, wherein the communication includes interactive control.

8. The system of claim 1, wherein the first user's device or the second user's device is at least one selected from the group of a smart phone, a personal computer, a wearable computing apparatus, and combinations thereof.

9. The system of claim 1, wherein the one or more input parameters corresponds to one or more time thresholds.

10. The system of claim 9, further configured to transfer the sensing data to the second user's device;
   wherein transferring the sensing data to the second user's device is stopped when a duration of transmitting the sensing data exceeds at least one of the one or more time thresholds, and the duration of transmitting the sensing data is a time of an interaction of the first user device with the second user device using the sensing data.

11. A method, comprising:

establishing a communication between a first user's device and a second user's device, wherein the first user's device is configured to broadcast a first live video while the second user's device is configured to receive the first live video through a broadcast platform, or the second user's device is configured to broadcast a second live video while the first user's device is configured to receive the second live video through the broadcast platform;

predefining one or more preset parameters using the first user's device;

determining whether one or more input parameters satisfies the one or more preset parameters, in response to the first user's device receiving the one or more input parameters from the second user's device, wherein when the one or more input parameters satisfies the one or more preset parameters, communicating, using a first sex toy, sensing data to the first user's device when the first sex toy is manipulated by a first user, wherein the sensing data is detected by at least one sensor integrated with the first sex toy, and wherein the first sex toy is configured to communicate with the first user's device and to be actuated by the first user's device or manipulated by the first user;

transmitting, by the first user's device, the sensing data to the second user's device;

receiving, by the second user's device, the sensing data from the first user's device; and actuating, by the second user's device, a second sex toy according to the sensing data as an interactive feedback, wherein the second sex toy is configured to communicate with the second user's device and to be actuated by the second user's device or manipulated by the first user, such that the second sex toy reacts to the manipulation of the first sex toy in real-time or in near real-time, wherein determining whether the one or more input parameters satisfies the one or more preset parameters includes:

establishing the communication in response to a certain amount of tips being transmitted from the first user's device to the second user's device, or from the second user's device to the first user's device.

12. The method of claim 11, wherein the sensing data includes at least one selected from the group of tactile data, pressure data, wobble data, temperature data, inserting depth data, and combinations thereof, the sensing data being sensed by the at least one sensor; and actuating the second sex toy includes actuating the second sex toy to perform at least one selected from the group of vibration, rotation, swinging, inhalation, temperature variation, contraction, reciprocation, and combinations thereof.

13. The method of claim 12, wherein the first sex toy or the second sex toy includes a female sex toy or a male sex toy, and manipulating the first sex toy or the second sex toy includes either:

inserting the female sex toy into a body part of the user; or inserting a body part of the user into the male sex toy.

14. The method of claim 12, wherein detecting the sensing data with the at least one sensor of the first sex toy includes determining a depth to which the first sex toy is inserted in a user's body, or to which a genital organ of the user's body is received in the first sex toy.

15. The method of claim 12, wherein actuating the second sex toy according to the sensing data as an interactive feedback includes:

based on a magnitude of the sensing data, actuating the second sex toy dynamically at different levels.

16. The method of claim 15, wherein based on the magnitude of the sensing data, actuating the second sex toy dynamically at different levels includes at least one selected from the group of:

as a magnitude of the pressure data or the wobble data increases, the more intensively the second sex toy is actuated;

as a magnitude of the temperature data increases, a temperature of the second sex toy increases; and combinations thereof.

17. A non-transitory computer-readable storage medium, comprising:

machine-readable instructions, wherein the machine-readable instructions when executed by a processor of a controller, cause the controller to:

establish a communication between a first user's device and a second user's device;

wherein the first user's device is configured to broadcast a live video through a broadcast platform and the second user's device is configured to receive the live video through the broadcast platform;

predefine one or more preset parameters using the first user's device;

determine whether one or more input parameters satisfies the one or more preset parameters, in response to the first user's device receiving the one or more input parameters from the second user's device, wherein when the one or more input parameters satisfies the one or more preset parameters, communicate, using a first sex toy, sensing data to the first user's device when the first sex toy is manipulated by a first user, wherein the sensing data is detected by at least one sensor integrated with the first sex toy;

wherein the first sex toy is configured to communicate with the first user's device, and be actuated by the first user's device or to be manipulated by the first user;

transmit, by the first user's device, the sensing data to the second user's device;

receive, by the second user's device, the sensing data from the first user's device; and actuate, by the second user's device, a second sex toy according to the sensing data as an interactive feedback, such that the second sex toy reacts to the manipulation of the first sex toy in real-time or in near real-time;

wherein the second sex toy is configured to communicate with the second user's device, and be actuated by the second user's device or to be manipulated by a second user; and wherein determining whether the one or more input parameters satisfies the one or more preset parameters includes establishing the communication in response to a certain amount of tips being transmitted from the first user's device to the second user's device, or from the second user's device to the first user's device.

* * * * *